United States Patent [19]

Morehouse

[11] 3,997,580

[45] Dec. 14, 1976

[54] SILICONE SULFATES

[75] Inventor: Edward L. Morehouse, New City, N.Y.

[73] Assignee: Union Carbide Corporation, New York, N.Y.

[22] Filed: Nov. 14, 1972

[21] Appl. No.: 306,294

Related U.S. Application Data

[60] Division of Ser. No. 26,130, April 6, 1970, Pat. No. 3,707,492, which is a division of Ser. No. 574,576, Aug. 24, 1966, abandoned, which is a continuation-in-part of Ser. No. 304,988, Aug. 27, 1963, Pat. No. 3,381,019.

[52] U.S. Cl. .................... 260/448.2 N; 252/8.7; 252/353; 252/358; 260/448.2 B
[51] Int. Cl. .................................... C07f 7/10
[58] Field of Search ............. 260/448.2 N, 448.2 B

[56] References Cited

UNITED STATES PATENTS

| | | |
|---|---|---|
| 3,507,897 | 4/1970 | Kanner et al. ............... 260/448.2 N |
| 3,513,183 | 5/1970 | Morehouse ................. 260/448.2 N |
| 3,531,507 | 9/1970 | Morehouse ................. 260/448.2 N |
| 3,660,452 | 5/1972 | Morehouse ................. 260/448.2 N |
| 3,707,492 | 12/1972 | Morehouse ................. 260/448.2 N |

*Primary Examiner*—Daniel E. Wyman
*Assistant Examiner*—Paul F. Shaver
*Attorney, Agent, or Firm*—Eugene C. Trautlein

[57] ABSTRACT

This invention claims novel siloxane sulfates characterized by a trivalent linking group between the sulfate group(s) and the silicon atom(s). Such trivalent linking groups can be derived from, for example, trimethylolpropane. The novel siloxanes are anionic surfactants and are capable of lowering the surface tension of water, in some cases, as low as 20 dynes/cm. They are useful as wetting agents for polyethylene, cotton and other substrates. They are also useful as emulsifiers, foaming agents and detergent.

17 Claims, No Drawings

SILICONE SULFATES

CROSS REFERENCE TO RELATED APPLICATIONS

This application is a division of application Ser. No. 26,130, filed Apr. 6, 1970 (now U.S. Pat. No. 3,707,492) which was a division of application Ser. No. 574,576, filed Aug. 24, 1966 (now abandoned) which was a continuation-in-part of application Ser. No. 304,988, filed Aug. 27, 1963 (now U.S. Pat. No. 3,381,019).

The compounds of this invention are siloxanes containing at least one sulfatoorganoxyalkylsiloxy unit of the formula:

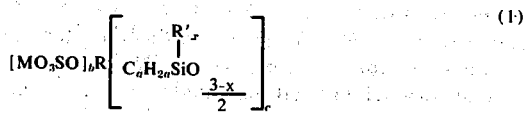
(1)

wherein M is a monovalent cation, $a$ is an integer of at least 2 and preferably from 2 to 4, $x$ is an integer of 0 to 2, $b$ and $c$ are as hereinafter defined, $R'$ is a monovalent hydrocarbon group having not more than 18 carbon atoms free of aliphatic unsaturation, R is a multivalent organic group selected from the class consisting of:

1. divalent, trivalent and tetravalent groups having the formula

(a)

wherein $R''$ is a monovalent group having not more than 19 carbon atoms selected from the class consisting of monovalent hydrocarbon groups free of aliphatic unsaturation, methylol, alkanoyloxymethyl, and alkenyloxymethyl, $b$ is an integer of 1 to 3, $c$ is an integer of 1 to 3 and $b+c$ is an integer of 2 to 4 and is equal to the valence of said R group;

2. acyclic divalent and trivalent groups having the formula:

(b)

wherein the Alkenyloxy group has not more than 6 carbon atoms, $b$ is an integer of 1 to 2, $c$ is an integer of 1 to 2, $b$ represents the number of carbon valences bonded to sulfate groups, and $b+c$ is an integer of 2 to 3 and is equal to the valence of said R group;

3. divalent polyoxyalkylene groups having the formula:

(c)

wherein $y$ is an integer of 2 to 4 and $p$ is an integer of 2 to 100, $b$ is 1 and $c$ is 1;

4. divalent groups having the formula:

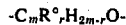
(d)

wherein $R°$ is a monovalent carbon-bonded hydrocarbon group having not more than 18 carbon atoms and free of aliphatic unsaturation, $m$ is an integer of 2 to 4, $r$ is an integer of 0 to $m$, $b$ is 1 and $c$ is 1; and 5. divalent groups having the formula:

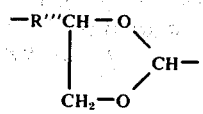
(e)

wherein $R'''$ is a divalent member of the class consisting of alkylene of 2 to 4 carbon atoms and alkyleneoxyalkylene wherein each alkylene moiety has 2 to 4 carbon atoms, $b$ is 1 and $c$ is 1; each said sulfate group $MO_3SO-$ being bonded to carbon of a carbon to carbon chain of said R group.

One class of compounds of this invention under formula (1) above includes siloxanes containing one or more unit of the formula:

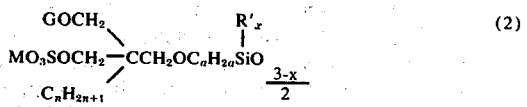
(2)

wherein G is hydrogen, $MO_3S-$, alkenyl or alkanoyl and preferably contains not more than 18 carbon atoms, $n$ is an integer of 1 to 19, preferably 1 to 10, $a$ is an integer of at least 2 and preferably 2 to 4, and M, $x$ and $R'$ are as defined above.

Another class of compounds under formula (1) includes siloxanes containing one or more unit of the formula:

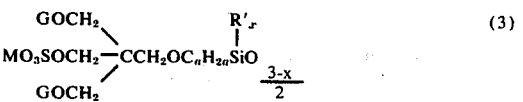
(3)

wherein G, M, $R'$, $a$ and $x$ have the above-defined meanings.

A further class of compounds under formula (1) includes siloxanes having one or more unit of the formula:

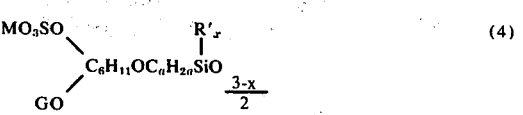
(4)

wherein G, M, $R'$, $a$ and $x$ have the above-defined meanings.

Another class of compounds under formula (1) includes siloxanes having one or more unit of the formula:

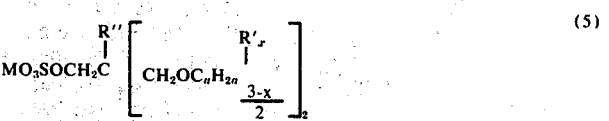
(5)

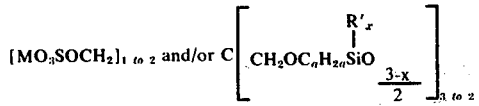

$$[MO_3SOCH_2]_{1\ to\ 2}\ \text{and/or}\ \left[\begin{array}{c}R'_r\\|\\CH_2OC_aH_{2a}SiO_{\frac{3-x}{2}}\end{array}\right]_{1\ to\ 2}$$
(6)

wherein M, R', R'', a and x have the above-defined meanings and R'' preferably is alkyl of not more than 10 carbon atoms, methylol, alkanolyoxymethyl, or alkenyloxymethyl of not more than 19 carbon atoms.

Another class of compounds under formula (1) includes siloxanes having one or more unit of the formula:

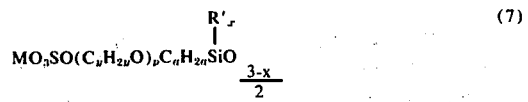

$$MO_3SO(C_yH_{2y}O)_pC_aH_{2a}SiO_{\frac{3-x}{2}}$$ (7)

wherein M, R', a and x have the above-defined meanings and y is an integer of 2 to 4 and p is an integer of 2 to 100. The integer y can be the same or different throughout the same unit. The designation $C_yH_{2y}O$ represents a chain made up of oxyalkylene units. When y is the same, the designation represents a polyoxyalkylene chain such as a polyoxyethylene or a polyoxypropylene chain. When y is different, the designation represents a mixed polyoxyalkylene chain such as a poly(oxyethyleneoxypropylene) chain. The mixed polyoxyalylene chain can contain the different oxyalkylene units in random distribution in the chain or it can contain blocks of several identical oxyalkylene units (e.g., oxyethylene units) joined to blocks made up of several identical oxyalkylene units of another type (e.g., oxypropylene units).

Another class of compounds under formula (1) includes siloxanes having one or more unit of the formula:

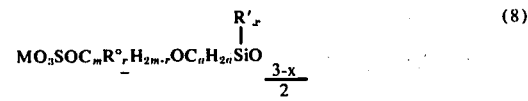

$$MO_3SOC_mR°_rH_{2m-r}OC_aH_{2a}SiO_{\frac{3-x}{2}}$$ (8)

wherein M, R', a and x have the above-defined meanings and R° is a monovalent hydrocarbon group of not more than 18 carbon atoms and free of aliphatic unsaturation, m is an integer of 2 to 4 and r is an integer of 0 to m.

Another class of compounds under formula (1) includes siloxanes having one or more unit of the formula:

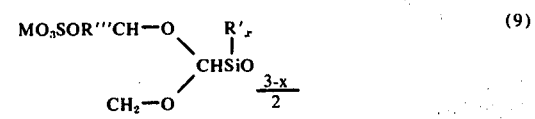

(9)

wherein M, R' and x have the above-defined meanings and R''' is alkylene or alkyleneoxyalkylene wherein each alkylene moiety has 2 to 4 carbon atoms.

Typical of the monovalent cations represented by M in the above formulas are ammonium, alkali metal, e.g., sodium, potassium, lithium, cesium and rubidium, alkyl or aryl substituted ammonium, e.g., triethylamine cation, $Et_3NH^+$, tetramethylammonium cation, $Me_4N^+$, and the like, Typical of the monovalent hydrocarbon groups represented by R', R'' and R° are the linear alky groups (e.g., methyl, ethyl, propyl and butyl groups), cyclic alkyl groups (e.g., cyclopentyl and cyclohexyl groups), the aryl groups (e.g., phenyl and naphthyl groups), the alkaryl groups (e.g., tolyl groups), and the aralkyl groups (e.g., the beta-phenylethyl group). Typical of the groups representing $C_aH_{2a}$ in the above formulas are the 1,2-ethylene, 1,3-propylene, 1,4-butylene, and 1,5-pentylene groups. Typical alkenyl groups represented by G and in the alkenyloxymethyl groups represented by R'' in the above formulas and in the Alkenyloxy groups of formula (b) above include allyl, methallyl, vinyl, butenyl, pentenyl and hexenyl groups. Alkanoyl groups represented by G and in the alkanoyloxymethyl group of R'' in the above formulas have the formula,

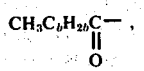

$$CH_3C_bH_{2b}\underset{\underset{O}{\|}}{C}-,$$

where b is an integer of 0 to 30. Typical alkanoyl groups include lauroyl, palmitoyl, stearoyl, n-caproyl, acetyl, propionyl, butyryl, isobutyryl, n-valeryl, capryl and isovaleryl. Alkylene groups represented by R''' and in the alkyleneoxyalkylene groups represented by R''' in the above formulas include ethylene, 1,3-propylene, 1,2-propylene, and 1,4-butylene and can be the same or different in each R''' group. In the novel compounds described above the M cations and the R', R'' and G groups may be the same as or different from other cations and respective groups throughout each unit or molecule. Likewise the groups R, R°, R''' and Alkenyloxy can be the same as or different from respective groups throughout each molecule. The integers a, b, c, x, y, p, m, n, and r can be the same or different from unit to unit.

In addition to the sulfatoorganoxyalkylsiloxy units, such as those represented by the above formulas, the siloxanes of this invention can also contain siloxy units represented by the formula:

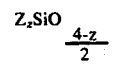

$$Z_zSiO_{\frac{4-z}{2}}$$ (10)

wherein Z represents a hydrogen atom, a monovalent hydrocarbon group free of aliphatic unsaturation such as defined for R' above or a monovalent polyoxyalkylene group of the formula $DO(C_yH_{2y}O)_sC_aH_{2a}$ wherein D is hydrogen, alkyl or phenyl, y is 2 to 4 and may be the same or different in each group, a is as defined above and s is 1 to 100 and z has a value from 0 to 3 inclusive and Z may be the same or different in each unit (10) and/or molecule and the integers a, y, z and s can be the same or different from unit to unit. Typical of the units represented by formula (10) are the $SiO_2$, monomethylsiloxy, dimethylsiloxy, trimethylsiloxy, monophenylsiloxy, methyl[butoxypoly-(oxyethyleneoxypropylene)propyl]siloxy, diphenylsiloxy, triphenylsiloxy, methyl(methoxypolyoxyethylenepropyl)siloxy, betaphenylethylsiloxy, methyl(hydrogen)siloxy and methyl(ethyl)-siloxy units. When present in the siloxanes of this invention, units represented by formula (10) are present in an amount from 1 to 99 mole % or preferably from 10 to 60 mole % with the balance of the units in the siloxane being sulfatoorganoxyalkylsiloxy groups as defined above.

The novel compounds of this invention can be produced by either of two reactions: (1) sulfation of carbon-bonded hydroxyl-containing siloxanes (hereinafter called silicone alcohols for simplicity) with mild sulfating agents, e.g., sulfamic acid or (2) addition of olefinically unsaturated organic ether or polyether sulfates (hereinafter called alkenyl organic ether sulfates for convenience) and hydrosiloxanes, i.e., siloxanes containing silanic hydrogen.

SULFATION

The sulfation referred to above can be illustrated by the equation:

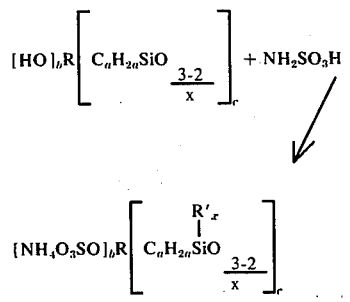

(1)

wherein R, R', a, b, c and x are as defined above.

The sulfating conditions used must be relatively mild. Some standard sulfating techniques customarily used to convert fatty organic alcohols to sulfates are not preferred in preparing compositions of this invention because they can cause undue cleavage of siloxane linkages and/or the ether linkages of the silicone alcohol. The strong sulfating agents which can cause cleavage include sulfuric acid, sulfur trioxide and, under certain conditions, chlorosulfonic acid. Useful sulfating agents include sulfamic acid and complexes of the stronger sulfating agents, including amine complexes, e.g., pyridine and other tertiary amine complexes, phosphorus complexes, e.g., tributyl phosphate complexes, and dimethylformamide, dioxane, and bis($\beta$-chloroethyl) ether complexes with $SO_3$. Strong sulfating agents can be useful only when the reaction mixtures are well buffered to avoid highly acidic conditions. For example, chlorosulfonic acid can sometimes be used if it is added to the silicone alcohol in the presence of a tertiary amine, or if by-product HCl is rapidly removed by some other means. The amount of sulfating agent is not narrowly critical but it is preferable to employ approximately one mole of sulfating agent for each mole of carbon-bonded hydroxyl group desired to be sulfated in the silicone alcohol.

Effective catalysts for sulfations with sulfamic acid are dimethylformamide and dimethylacetamide. These also can perform the function of solvent. Other amides, e.g., urea, are useful catalysts. Preferably the catalyst should be present at a concentration of 0.5% or higher and when the catalyst doubles as a solvent, its concentration can be higher, these concentrations being based on the total weight of the reaction mixture.

In the synthesis of the novel compounds of this invention, solvents are not always necessary but they may aid in increasing compatibility between reactants. Amides are excellent solvents in sulfations with sulfamic acid and, as pointed out above, they also function as catalysts. Dimethylformamide and dimethylacetamide are particularly effective. Sometimes halogenated hydrocarbons, aromatic hydrocarbons and ethers are desirable as solvents in processes of this invention. The amount of solvent used is not narrowly critical and depends upon the handling and compatibility characteristics desired. As an illustration, 10 to 1000 weight parts solvent per 100 weight parts of total reactants can be used.

Preferred reaction temperatures for sulfations with sulfamic acid using a catalyst are 85°–95° C. Lower temperatures are impractically slow; higher temperatures may be used but appear to offer no advantage. In the absence of a catalyst, the preferred temperature range is 110°–140° C. Lower temperatures are impractically slow; higher temperatures seriously cleave ether or siloxane chains.

Preferred reaction temperatures for sulfations with chlorosulfonic acid are about 0° to 40° C. Lower temperatures are unnecessary; higher temperatures may lead to serious cleavage of ether or siloxane chains.

The above-described sulfation conditions can be employed to sulfate olefinically unsaturated organic ether or polyether alcohols (hereinafter called alkenyl organic ether alcohols for simplicity) used to produce the starting materials in the second named reaction, i.e., the addition of alkenyl organic ether sulfates and hydrosiloxanes. Such sulfations are depicted by the equation:

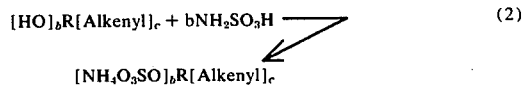

(2)

wherein R, b and c are as defined above and Alkenyl is an alkenyl group having at least 2 and preferably 2 to 4 carbon atoms. Typical alkenyl organic ether alcohols include the monoallyl ethers of ethylene glycol, diethylene glycol, triethylene glycol, polyoxyethylene glycols having up to 100 oxyethylene units, poly(oxyethyleneoxypropylene) glycols containing up to 100 oxyethylene and oxypropylene units in random distribution, trimethylolpropane, pentaerythritol, 1,2,6-hexanetriol, 2,2-dimethyl-1,3-propanediol, trimethylolmethylbenzene, 2-phenyl-2-methylolpropanol, 2-methyl-2-methylolpropanol; the diallyl ether of trimethylolpropane, pentaerythritol, trimethylolmethylbenzene, and 1,2,6-hexanetriol; triallyl ether of pentaerythritol; 2-vinyl-4-hydroxybutyldioxolane; 2-vinyl-4-(2-hydroxypropoxybutyl)dioxolane, acrolein-pentaerythritol condensates and methacroleinpentaerythritol condensates.

In sulfations of silicone alcohols and olefinically unsaturated organic ether or polyether alcohols it is convenient to mix all of the sulfamic acid with the alcohol and heat to the chosen reaction temperature. Optionally, either reactant can be added to the other in increments while maintaining the chosen reaction temperature. In the case of chlorosulfonic acid, a stronger sulfating agent, sulfation should be accomplished by slow addition of the acid to the alcohol. By-product HCl is preferably removed by simultaneous sparging, use of reduced pressure or by an acid acceptor such as an amine. More powerful sulfating agents per se such as sulfur trioxide and sulfuric acid have limited application in synthesizing the novel compounds of this invention, or the intermediates used in making them, because of cleavage of ether or siloxane linkages. However, complexes of such sulfating agents (e.g., amine complexes) can be employed.

The silicone alcohols used as starting materials for the sulfation reaction described above can be prepared by the addition of alkenyl organic ether alcohols of the formula $[HO]_bR[Alkenyl]_c$ (11) as described and typified above and hydrosiloxanes using the addition reaction conditions hereinafter described. The preparation of certain such silicone alcohols is also described in the copending application.

The alkenyl organic ether alcohols used as starting materials in the sulfation described above and in the addition reaction hereinafter described are readily prepared by known methods. For example, to form the monoallyl ethers listed after equation (2) above, the specified organic alcohol (i.e., ethylene gylcol, diethylene glycol, etc.) is reacted with substantially equimolar amounts or less of NaOMe to first form the monoalkoxide which is then reacted with allyl chloride to result in the monoallyl ether of the specified organic alcohols, which then can be separated in relatively pure condition. NaOH can be employed, if desired. To form the diallyl ethers listed after equation (2) above, the respective specified organic alcohol (i.e., trimethylolpropane, pentaerythritol, etc.) is reacted with greater than equimolar amounts based on the respective functional groups, e.g., up to 2:1, of NaOMe to first form the dialkoxide which is then reacted with allyl chloride to result in the diallyl ether which then can be separated in relatively pure condition. The triallyl ethers listed after equation (2) above are formed by reacting the specified organic alcohol (e.g., pentaerythritol) with 2 to 3 moles NaOMe per mole alcohol to first form the trialkoxide which then is reacted with allyl chloride to result in the triallyl ether which then can be separated in relatively pure condition,

ADDITION REACTION

The addition reaction between an alkenyl organic ether sulfate and a hydrosiloxane can be depicted by the equation:

$[MO_3SO]_bR[Alkenyl]_c + cHSi(R')_xO_{\frac{3-x}{2}}$ (3)

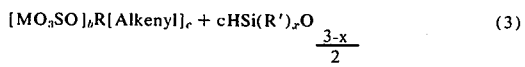

wherein M, R, R', Alkenyl, a, b and c are as defined above.

The addition reaction between an alkenyl organic ether alcohol and hydrosiloxane in preparing the silicone alcohol starting materials for sulfation can be depicted by the equation:

$[HO]_bR[Alkenyl]_c + cHSi(R')_xO_{\frac{3-x}{2}}$ (4)

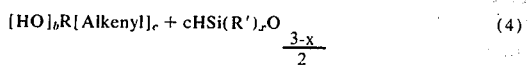

wherein M, R, R', Alkenyl, a, b and c are as defined above.

In general, the reactions illustrated by equations (3) and (4) can be conducted employing, preferably, from 10 to 20 parts, per million parts by weight of the reactants, of platinum, e.g., in the form of chloroplatinic acid dissolved, if desired, in a solvent such as tetrahydrofuran, ethanol, butanol or a mixture of ethanol and ethylene glycol dimethyl ether, or in the form of finely divided elemental platinum supported on a material such as gamma alumina or charcoal. The addition reactions are conducted at a temperature of from 60° C. to 200° C., or preferably at a temperature from 70° C. to 130° C. It is preferred to conduct the reactions in the presence of a liquid organic compound or solvent in which the reactants are mutually soluble. Solvents are especially preferred in reaction (3) so as to provide greater compatibility between the highly polar sulfate and the relatively non-polar hydrosiloxane. Suitable solvents include alcohols (e.g., ethanol and isopropanol) and aromatic hydrocarbons (e.g., toluene and xylene) and ethers (e.g., ethylene glycol diethyl ether, diethylene glycol dimethyl ether, diisopropyl ether, and dipropyl ether). Such solvents are employed in an amount from 10 parts to 1000 parts by weight per 100 parts by weight of the reactants.

The relative amounts of the alkenyl organic ether sulfate or alcohol and the hydrosiloxane employed in producing the siloxanes of this invention are not narrowly critical. A slight excess of alkenyl organic ether sulfate or alcohol, e.g., 10% excess, is advantageous from the standpoint of more effective and more complete reaction of silanic hydrogen. In those cases where it is desired to preserve some of the alkenyl groups in the alkenyl organic ether sulfate or alcohol (e.g., where it is desired to produce a siloxane of formula (1) wherein R is of formula (a) and R'' is alkenyloxymethyl, or a siloxane of formula (2), (3) or (4) wherein G is alkenyl, or a siloxane of formula (5) wherein R'' is alkenyloxymethyl), it is desirable to employ amounts of the alkenyl organic ether sulfate or alcohol that provide a substantial stoichiometric excess of alkenyl groups. Similarly in those cases where an alkenyl organic ether sulfate or alcohol containing more than one alkenyl group is employed and it is desired to minimize cross-linking of siloxane molecules, a large excess of the alkenyl organic ether sulfate or alcohol can be employed.

The order in which the alkenyl organic ether sulfate or alcohol, the hydrosiloxane and the platinum catalyst are mixed in forming a reaction mixture for use in producing the siloxanes of this invention is not critical. The catalyst can be added separately to the alkenyl organic ether sulfate or alcohol or to the siloxane or can be added to a mixture of these materials. In reaction (4), it is preferable to add the siloxane to the alkenyl organic ether alcohol in increments since this technique minimizes any side reactions (e.g., reaction between the silanic hydrogen and the COH groups of alkenyl ether) which may occur to some extent. This technique of addition also aids in controlling the reactions, some of which are often exothermic. Additional catalyst can be added during the course of the reaction in the event the rate of reaction decreased (e.g., due to catalyst poisoning).

Alkenyl organic ether sulfates used as starting materials in equation (3) can be prepared by the reaction illustrated by and described in conjunction with equation (2) and are typified by the following: $NH_4O_3SOC_2CH=CH_2$, $NaOp_3SOC_2H_4OCH_2CH=CH_2$, $NaO_3SOC_2H_4OC_2H_4OCH_2CH=CH_2$, $NH_4O_3SOC_2H_4OC_2H_4OCH_2CH=CH_2$; $NH_4O_3SO(C_2H_4O)_nOCH_2CH=CH_2$ where n averages respectively 4, 6, 9, 13, 22, 35 and 67, $NaO_3SO(C_3H_6O)_nOCH_2CH=CH_2$ where n averages respectively 2, 7, 17 and 40, $NaO_3SO(C_3H_6O)_{14}-(C_2H_4O)_{14}OCH_2CH=CH_2$, $(NH_4O_3SOCH_2)_2C(ET)CH_2OCH_2CH=CH_2$, $(NH_4O_3SOCH_2)_3CCH_2OCH_2CH=CH_2$, $(NH_4O_3SO)_2C_6H_{11}OCH_2CH=CH_2$, $(NH_4O_3SOCH_2)_2C(Me)CH_2OCH_2CH=CH_2$, $(NaO_3SOCH_2)_2C(C_6H_5)CH_2OCH_2CH=CH_2$, $NaO_3SOCH_2C(Me)(C_6H_5)CH_2OCH_2CH=CH_2$, $NaO_3SOCH_2C(Me)_2CH_2OCH_2CH=CH_2$, $NH_4O_3SOCH_2C(Et)(CH_2OCH_2CH=CH_2)_2$, $(NH_4O_3SOCH_2)_2C(CH_2OCH_2CH=CH_2)_2$, $NH_4O_3SOCH_2C(C_6H_5)(CH_2OCH_2CH=CH_2)_2$, $NaO_3SOCH_2C(Me)(CH_2OCH_2CH=CH_2)_2$, $NaO_3SOC_6H_{11}(OCH_2CH=CH_2)_2$, $NH_4O_3SOCH_2C(CH_2OCH_2CH=CH_2)_3$, $NH_4O_3SO(CH_2)_4$-

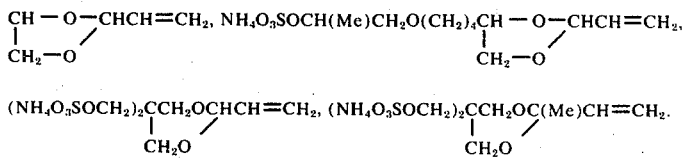

The hydrosiloxanes employed in producing the siloxanes of this invention contain the group represented by the formula:

$$HSiO_{\frac{3-x}{2}}^{R'_x} \quad (12)$$

wherein R' and x have the above-defined meanings. Such starting siloxanes can also contain groups represented by formula (10).

At the conclusion of the reactions illustrated by equations (3) and (4), the siloxane of this invention produced as a product can be isolated from the reaction mixture by conventional means. When chloroplatinic acid is used as a catalyst, acidic compounds are formed which are preferably neutralized with a basic compound (e.g., sodium bicarbonate) before isolating the siloxane. Suitable means for isolating the siloxane include sparging the reaction mixture by passing an inert gas (e.g., nitrogen) through the reaction mixture which is maintained at an elevated temperature (e.g., a temperature up to 170° C.) to volatilize any unreacted volatile starting materials. The insoluble catalyst and any insoluble by-product can be conveniently removed by filtration. Fractional distillation can be employed where the siloxane is relatively volatile. In those cases where the siloxane or the siloxane-solvent solution is immiscible with the reactants, separation can be achieved by decantation or use of a separatory funnel.

The above-described addition reactions producing the siloxanes of this invention are remarkably efficient, particularly when allyl organic ether sulfate or alcohol starting materials are employed, as compared to seemingly analogous reactions involving allyl alcohol. Specifically, when allyl alcohol is reacted with a hydrosiloxane, the reaction of the COH group of the alcohol with silanic hydrogen occurs to a significant extent and may even be the predominant reaction. On the other hand, when alkenyl (particularly allyl) organic ether sulfates or alcohols are employed as described above is producing the siloxanes of this invention, little reaction between the COH groups in the alkenyl starting material and the silanic hydrogen occurs. Moreover, the reaction of such allyl organic ether sulfates or alcohols with hydrosiloxanes to produce siloxanes of this invention is extremely rapid as compared to the sluggish reactions of this type heretofore known.

The novel siloxanes are excellent anionic surfactants and are capable of greatly lowering the surface tension of water, in some cases, as low as 20 dynes/cm. In some instances the surface tension lowering ability and wetting power of the novel siloxanes are superior to corresponding organic anionic surfactants. They are useful as powerful wetting agents for polyethylene, cotton and many other substrates. They are also useful as emulsifiers, foaming agents and detergent.

Aqueous solutions of the water-soluble novel siloxanes exhibit very low surface tensions and are useful in a variety of applications, e.g., the production of treating baths in the textile industries in wetting a wide variety of substrates including polyethylene, cotton, synthetic fibers (e.g., Fortrel, Dacron, Kodel, etc.), blends of cotton and synthetic fibers, etc.; in the production of emulsions for use in making polishes and waxes for floors, automobiles, furniture, etc.; in the production of cleaning solutions and so on. Such aqueous solutions can contain as little as 0.01 weight % and up to 20% or the solubility concentration of the novel siloxane; however, in the usual case, amounts of 0.05 to 1 weight % are useful for providing the surface tension lowering effects desired. The aqueous solutions can contain other water-soluble or water-miscible solvents such as lower alkanols including methanol, ethanol, propanol, isopropanol and tertbutanol for a variety of purposes including to promote greater solubility of the novel siloxane or other components of the solution.

The following examples are presented in which Me represents methyl, Et represents ethyl, all refluxing was done at ambient pressure and all parts and percentages are on a weight basis, unless otherwise specified.

EXAMPLE 1

A solution of 2-allyloxyethanol (102.1 g., 1.0 mole) in 200 g. of toluene in a one liter flask was heated to reflux and traces of water removed by azeotropic distillation. Chloroplatinic acid (0.018 milli-moles of platinum) was added. Simultaneously from two dropping funnels, 3-hydroheptamethyltrisiloxane (222.5 g., 1.0 mole) and 2-allyloxyethanol (10.2 g., 0.1 mole) containing chloroplatinic acid (0.012 millimoles of platinum) were added dropwise to the solution over a period of 1½ hours while maintaining the reaction temperature at 100°–115° C. The resulting reaction mixture was maintained at 110° C. for three hours longer, then fractionated by distillation. At 70°–75° C. and 0.03–0.05 mm. of Hg, the liquid silicone alcohol $Me_3SiO[HOC_2H_4OC_3H_6SiMeO]SiMe_3$ was obtained.

The above silicone alcohol (71.0 g., 0.218 mole), sulfamic acid (23.3 g., 0.24 mole) and 150 g. of N,N-dimethylformamide in a 500 ml. flask were heated for 3 hours at 85° C. Ammonia gas was bubbled through the reaction mixture to neutralize small amounts of residual acids. The mixture then was filtered and solvent removed by heating up to 80° C. at reduced pressure. The product was a silicone sulfate of composition $Me_3SiO[NH_4O_3SOC_2H_4OC_3H_6SiMeO]SiMe_3$. It was an extremely viscous liquid which was soluble in water.

This silicone sulfate was very surface active, as shown by the following test results:

| A. Aqueous Surface Tensions (duNouy Method): | |
|---|---|
| Wt–% Silicone | Dynes/cm. |
| 1.0 | 20.1 |
| 0.1 | 21.6 |
| 0.01 | 37.3 |

B. Wetting of Polyethylene

A droplet (0.02 ml.) of an aqueous solution of one wt-% silicone sulfate was applied by syringe to a clean sheet of polyethylene. Within three minutes the diameter of the droplet had increased over 300%. This order of wetting of polyethylene is greater than has been observed with organic anionics.

C. Emulsification

A stable emulsion was formed when 4.0 g. of benzene, 6.0 g. of water and about 0.5 g. of the silicone sulfate were shaken together.

EXAMPLE 2

An allylated polyether of average composition $CH_2=CHCH_2(OC_2H_4)_{16}OMe$ (298 g., 0.38 mole); the monoallyl ether of trimethylolpropane (53.8 g., 0.31 mole) and 375 ml. of toluene were weighted into a two-liter flask fitted with mechanical stirrer, thermometer and condenser. The mixture was heated to reflux, chloroplatinic acid (0.15 milli-moles of Pt) was added and a hydrosiloxane of average composition $Me_3SiO(Me_2SiO)_{8.5}(MeHSiO)_{3.5}SiMe_3$ (148.2 g., 0.52 mole of silanic hydrogen) was added dropwise. The resulting mixture was refluxed and when the amount of residual silanic hydrogen had become very low, as noted by external silver tests, the reaction mixture was sparged with nitrogen at 130° C. The product (441 g.) was a liquid silicone alcohol having the approximate composition $Me_3SiO[Me_2SiO]_{8.5}[(HOCH_2)_2-C(Et)CH_2OC_3H_6SiMeO]_{1.75}[Me-(OC_2H_4)_{16}OC_3H_6SiMeO]_{1.75}SiMe_3$.

The above silicone alcohol (50 g., 0.059 mole of OH), sulfamic acid (5.3 g., 0.055 mole) and 0.15 g. of urea, as catalyst, were stirred together for 2 hours at 90° C. Analysis at this point showed that at least 88% of the sulfamic acid had reacted. The reaction mixture was neutralized with gaseous ammonia, then sparged briefly with nitrogen. The product was a silicone sulfate of the approximate composition $Me_3SiO[Me_2SiO]_{8.5}[(NH_4O_3SOCH_2)_2C(C_2H_5)CH_2OC_3H_6SiMeO]_{1.75}[Me-(OC_2H_4)_{16}OC_3H_6SiMeO]_{1.75}SiMe_3$. It was a liquid with a viscosity of 60,000 centistokes. A one percent aqueous solution of this silicone sulfate had no cloud point up to 100° C. The solution was clear and remained so after boiling two hours. The surface tension of this solution at 25° C. was 34.6 dynes/cm.

EXAMPLE 3

The monoallyl ether of trimethylolpropane (190 g., 1.1 moles), stearic acid (310 g., 1.1 moles), 5 g. of concentrated sulfuric acid and 500 ml. of toluene were heated together and water removed by azeotropic distillation. The theoretical amount of water for formation of the monostearate (19 g.) was removed. The reaction mixture was neutralized with sodium bicarbonate, filtered and desolvated by nitrogen sparging to 130° C. The product, having the average composition of the monostearate, was a waxy solid at room temperature.

The above monostearate (172 g., 0.38 mole) and 200 ml. of toluene were heated together to reflux, 0.022 milli-mole of platinum was added as chloroplatinic acid, and then a siloxane of the average composition $Me_3SiO[Me_2SiO]_{8.5}-[MeHSiO]_{3.5}SiMe_3$ (77 g., 0.27 mole SiH) was added dropwise while refluxing. When tests showed that essentially all of the SiH had reacted, the reaction mixture was sparged with nitrogen at 130° C. The silicone alcohol thus produced was a waxy solid at room temperature having the following analysis:

Anal.: Br No., 3.8 OH (as COH), 1.4%

This confirmed the silicone alcohol as containing units of the formula $[(HOCH_2)(C_{17}H_{35}COOCH_2)C(C_2H_5)CH_2OC_3H_6SiMeO]$.

The above silicone alcohol (50 g., 0.069 mole OH) and sulfamic acid (6.7 g., 0.069 mole) were dissolved in 30 g. of N,N-dimethylformamide and the solution heated and maintained at 85°–95° C. for an hour. After this time, titration of an aliquot showed that more than 90% of the sulfamic acid had reacted. The reaction mixture was neutralized with gaseous ammonia, filtered and sparged at 130° C. with nitrogen containing a little ammonia. The solid product (57.8 g.) was mostly a silicone sulfate of approximate average composition $Me_3SiO[Me_2SiO]_{8.5}[(NH_4O_3SOCH_2)(C_{17}H_{35}COOCH_2)C(C_2H_5)CH_2OC_3H_6SiMeO]_{3.5}SiMe_3$.

Anal.: OH (as COH), 0.5 N, 2.1 S, 3.8

EXAMPLE 4

To a solution of the diallyl ether of trimethylolpropane (91 g., 0.43 mole), 200 ml. of toluene and 0.042 millimole of platinum (as chloroplatinic acid) at reflux was added 3-hydroheptamethyltrisiloxane, $Me_3SiOMeHSiOSiMe_3$, (121 g., 0.55 mole) dropwise. The reaction mixture was desolvated by sparging with nitrogen at 130° C. The resulting silicone alcohol was a liquid having a viscosity of 25 centistokes, OH content of 2.2% and mainly comprised $[(Me_3SiO(_2Si(Me)C_3H_6OCH_2]_2-C(Et)(CH_2OH)$.

This silicone alcohol (85.9 g., 0.11 mole of OH) and sulfamic acid (14.1 g., 0.14 mole) were dissolved in 100 g. of N,N-dimethylformamide. The solution was heated at 85°–90° C. for 45 minutes. Ammonia gas was passed through the solution until the reaction mixture was alkaline and precipitated salts were removed by filtration. The filtrate was stripped at reduced pressure.

The semi-solid product was mainly an ammonium silicone sulfate of composition [(Me₃SiO)₂Si(Me)-C₃H₆OCH₂]₂C(C₂H₅)(CH₂OSO₃NH₄). It was insoluble in water and had the following analysis:

Calc.: N, 1.9; Si, 22.3; S, 4.2 Found: N, 2.2; Si, 16.2; S, 4.3; OH, 0.2

It was useful in making water-in-oil (water-in-benzene) emulsions.

EXAMPLE 5

A polyether of approximate composition CH₂=CHCH₂-O(C₂H₄O)₁₉(C₃H₆O)₁₄H (200 g., 0.12 mole of OH) was weighed into a 500 ml. flask fitted with stirrer, thermometer, sparge tube and dropping funnel. Chlorosulfonic acid (13.7 g., 0.12 mole) was added dropwise to the polyether at 25° C. A rapid stream of nitrogen was introduced during sulfation to remove by-product HCl. The resulting polyether acid sulfate was converted to the sodium salt by reaction with aqueous sodium hydroxide. Water was removed by azeotropic distillation with toluene. Decolorizing carbon and a filter aid (Hy Flo Super Cel) were added and the reaction mixture filtered. The filtrate was sparged with nitrogen. There resulted a polyether sulfate sodium salt of the following description:

Properties:
Viscosity, cstks. at 25° C.     1400
1% Aqueous Cloud Point, ° C.     72
Anal.:
Found: Na, 0.9; S, 1.3; Cl, 0.05; Br. No., 7.8
Approximate Composition:
CH₂=CHCH₂O(C₂H₄O)₁₉(C₃H₆O)₁₄SO₃Na A hydrosiloxane of average composition Me₃SiO(Me₂SiO)₂₀(MeHSiO)₃.₂SiMe₃ (19.7 g., .034 mole SiH), 75 g. of toluene and 0.036 milli-equivalents of Pt as chloroplatinic acid, were heated to 70°–80° C. A mixture of the polyether sulfate sodium salt (80 g., .039 mole), 75 g. of toluene and 0.015 milli-equivalents of platinum as chloroplatinic acid was added dropwise. the reaction mixture was desolvated by sparging with nitrogen. The product was a silicone polyether sulfate of the following characteristics:

Properties:
Viscosity, cps. at 25° C.     15,000
1% Aqueous Cloud Point, ° C.     >100° C.
Aqueous Surface Tension     Dynes/cm. at 25° C.
Conc. of Surfactant (wt-%)
    1.0     30.8
    0.1     33.2
    0.01     41.7
    0.001     53.3
Anal.:
Found: Na, 0.65; S, 1.0; Si, 7.0
Approximate Composition:
Me₃SiO[NaO₃SO(C₂H₄O)₁₉(C₃H₆O)₁₄C₃H₆SiMeO]₃.₂-

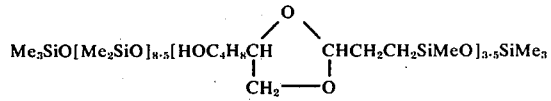
[Me₂SiO]₂₀SiMe₃

EXAMPLE 6

A silicone alcohol of average composition

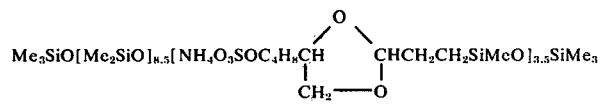

(40 g., 0.09 mole OH), prepared in the manner described in the copending application, and sulfamic acid (9.8 g., 0.1 mole) were dissolved in 50 g. of N,N-dimethylformamide. The solution was heated at 85° C. for 15 minutes. More N,N-dimethylformamide was added to reduce the viscosity. The solution was made alkaline with ammonia gas, filtered and stripped at reduced pressure. The product was a silicone sulfate of the following approximate average composition:

Me₃SiO[Me₂SiO]₈.₅[NH₄O₃SOC₄H₈CH(CH₂—O)CHCH₂CH₂SiMeO]₃.₅SiMe₃

It was a red, water-soluble oil. The silicone alcohol starting material was not soluble in water.

EXAMPLE 7

A silicone alcohol of composition Me₃SiOMe₂SiC₃H₆OCH₂C(C₂H₅)(CH₂OH)₂ (25 g., 0.08 mole) prepared by reacting Me₃SiOMe₂SiH with the monoallyl ether of trimethylolpropane in the presence of chloroplatinic acid catalyst, and sulfamic acid (18 g., 0.19 mole) were added to 61 g. of N,N-dimethylformamide. The reaction mixture was heated for 2 hours at 85° C., made alkaline with gaseous ammonia and filtered. After desolvating the filtrate at reduced pressure, a semi-solid silicone sulfate was obtained. It was mainly of the composition Me₃SiOMe₂SiC₃H₆OCH₂C(C₂H₅)(CH₂OSO₃NH₄)₂ and had the following characteristics:

Properties

A. Aqueous surface tensions compared with sodium dodecyl benzene sulfonate, NaDBS ("Trepolate F-95"):

| Surfactant | Dynes/cm. at 25° C. at indicated wt-% Surfactant | | |
|---|---|---|---|
| | 1.0% | 0.1% | 0.01% |
| Silicone sulfate | 21.6 | 26.5 | 52.3 |
| NaDBS | 29.6 | 31.8 | 41.9 |

B. Wetting, Synthron Tape Method: 4.1 seconds at 1.0 wt-%.

C. Anal.: Found: N, 8.5; S, 11.4; Si, 5.4.

D. The foaming properties and stability of this silicone sulfate, at a concentration of one weight percent in water at pH 7, are shown in the following table:

| Aging Time, Days | Foam Hgt., mm., Ross-Miles at 25° C. | |
|---|---|---|
| | Initial | 5 Min. |
| 0 | 155 | 155 |
| 1 | 153 | 152 |
| 4 | 150 | 148 |
| 6 | 151 | 150 |

EXAMPLE 8

A silicone alcohol (100 g., 0.41 mole OH) obtained by reaction of 3-hydro-heptamethyltrisiloxane with the monoallyl ether of trimethylolpropane in the presence of chloroplatinic acid catalyst, sulfamic acid (58 g., 0.60 mole) and 159 g. of N,N-dimethylformamide were stirred together in a flask for ½ hour at 85° C. The reaction product was made alkaline with gaseous ammonia and filtered. Solvent was removed from the filtrate leaving a water-soluble silicone sulfate. It had following followign approximate average composition:

$Me_3SiO[(NH_4O_3SOCH_2)_2C(C_2H_5)CH_2OC_3H_6SiMeO]SiMe_3$

The surface tension of a 1% aqeuous solution of this sulfate was 22.7 dynes/cm. at 25° C. Wetting time for this solution, by the Synthron Tape method, was 2.6 seconds at 25° C.

EXAMPLE 9

A copolymer of the composition $Me_3SiO[Me_2SiO]_{20}[HOCH_2CH_2OC_3H_6SiMeO]_2[C_4H_9(OC_2H_4)_{19}(OC_3H_6)_{14}OC_3H_6SiMeO]_4SiMe_3$ was prepared by reacting a hydrosiloxane of the composition $Me_3SiO[Me_2SiO]_{20}[HMeSiO]_6SiMe_3$ (0.03 mole SiH) with the monoallyl ether of the formula $C_3H_5O(C_3H_6O)_{14}(C_2H_4O)_{1.9}OC_4H_9$ (0.02 mole) in the presence of chloroplatinic acid catalyst. This copolymer (100 g., 0.22 mole of OH) and sulfamic acid (2.5 g., .026 mole) were stirred together and heated at 85° c. for 25 minutes. The reaction mixture was nuetralized with gaseous ammonia and filtered. The brown filtrate was a silicone sulfate having the approximate average composition $Me_3SiO[Me_2SiO]_{20}[NH_4O_3SOCH_2CH_2OC_3H_6SiMeO]_2[C_4H_9O(C_2H_4)_{19}(C_3H_6O)_{14}C_3H_6SiMeO]_4SiMe_3$. An aqueous solution of one weight percent of this anionic surfactant had a surface tension of 26.2 dynes/cm. and no cloud point up to 100° C. The non-sulfated intermediate had a cloud point of 31° C.

EXAMPLE 10

A copolymer of composition $Me_3SiO[Me_2SiO]_9[(HOCH_2)_2C(C_2H_5)CH_2OC_3H_6SiMeO]_{5.6}[CH_3(OC_2H_4)_7OC_3H_6SiMeO]_{5.6}SiMe_3$ was prepared by reacting a hydrosiloxane of the composition $Me_3SiO[Me_2SiO]_9[HMeSiO]_{11.2}SiMe_3$ (0.06 mole SiH) with the monoallyl ether of trimethylolpropane (0.03 mole) and the monoallyl monomethyl ether of polyoxyethylene having the formula $C_3H_5O(C_2H_4O)_7CH_3$ (0.03 mole) in the presence of chloroplatinic acid catalyst. This copolymer (150 g., 0.36 mole of OH) and sulfamic acid (35 g., 0.36 mole) were stirred together and heated at 110° C. for 30 minutes. The reaction product was made alkaline with gaseous ammonia and sparged with nitrogen to remove excess ammonia. The product, a silicone sulfate having the approximate average composition $Me_3SiO[Me_2SiO]_9[(NH_4O_3SOCH_2)_2C(C_2H_5)CH_2OC_3H_6SiMeO]_{5.6}[CH_3(OC_2H_4)_7OC_3H_6SiMeO]_{5.6}SiMe_3$, had no aqueous cloud point up to 100° C. The non-sulfated intermediate had a broad aqueous clouding range of 0°–30° C.

EXAMPLE 11

A solution of sulfamic acid (8.3 g., .086 mole) in 50 milliliters of N,N-dimethylformamide was added dropwise to an agitated solution of a silicone alcohol of composition $Me_3SiO[Me_2SiO]_{8.5}[(HOCH_2)_2C(C_2H_5)CH_2OC_3H_6SiMeO]_{3.5}SiMe_3$ (20 g., .087 mole OH), prepared in the manner described in the copending application, in 20 milliliters of N,N-dimethylformamide at 120° C. After completion of the addition, agitation at this temperature was continued ½ hour. The reaction mixture was neutralized with sodium bicarbonate and filtered. An aliquot of the filtrate (50 g.) was desolvated at reduced pressure. Fifteen grams of a soft, waxy silicone sulfate were obtained having the approximate average composition $Me_3SiO[Me_2SiO]_{8.5}[(NH_4O_3SOCH_2)_2C(C_2H_5)CH_2OC_3H_6SiMeO]_{3.5}SiMe_3$. This was essentially a 100% yield. The surface tension of a one weight percent solution of this surfactant in water was 30.7 dynes/cm. at 25° C.

EXAMPLE 12

A silicone alcohol, obtained by platinum-catalyzed addition of a hydrosiloxane of composition $Me_3SiO[Me_2SiO]_{8.5}[MeHSiO]_{3.5}SiMe_3$ to the monoallyl ether of trimethylolpropane (50 g., 0.21 mole OH) and 200 ml. of triethylamine were stirred together in a flask. Chlorosulfonic acid (16.6 g., 0.14 mole) was added dropwise. The temperature of the reaction mixture was maintained at 30°–40° C. by external cooling. Five hundred milliliters of acetone were added and the mixture filtered. The filter cake was washed with more acetone and dried. This cake (16 g.) was triethylamine hydrochloride.

The filtrate was placed in an evaporating dish and desolvated at room temperature. Two liquid layers formed. The upper layer was stripped at reduced pressure to constant weight. The product (53 g.), a viscous fluid, was a triethylamine silicone sulfate having the approximate average composition $Me_3SiO[Me_2SiO]_{8.5}[((C_2H_5)_3NHO_3SOCH_2)_2C(C_2H_5)CH_2OC_3H_6SiMeO]_{3.5}SiMe_3$. It was soluble in water-ethanol (80–20 by volume) and was a profoamer.

EXAMPLE 13

The low aqueous surface tensions and the good wetting characteristics of the silicone sulfates produced herein are shown in the following table wherein the percentages given are weight percents of the sulfate in water:

| Product of Example No. | Aqueous Surface Tension, dynes/ cm. at 25° C. | | | % Aqueous Wetting of Polyethylene 1% Solution (a) | Wetting, sec., Synthron Tape Method, 1% Aqueous Solution (b) |
|---|---|---|---|---|---|
| | 1.0% | 0.1% | 0.01% | | |
| 1 | 20.1 | 21.6 | 37.3 | >300 | 1 |
| 7 | 21.6 | 26.5 | 52.3 | 83 | 4 |
| 8 | 22.7 | 28.8 | 47.0 | 206 | 3 |
| 11 | 30.7 | 31.8 | 41.9 | 31 | 40 |
| Sodium Lauryl Sulfate (c) | 32.9 | 30.4 | 38.2 | 38 | 3 |

(a) Per cent increase in drop diameter after 3 minutes.
(b) Wetting time for distilled water was 950 seconds.
(c) "Duponol C".

The silicone sulfates were particularly effective wetting agents for relatively low energy surfaces such as polyethylene.

EXAMPLE 14

Sulfamic acid (7.8 g., .08 mole) was dissolved in 80 g. of N,N-dimethylformamide. A silicone alcohol of composition $Me_3SiO[HO(C_2H_4O)_3C_3H_6SiMeO]SiMe_3$ (30 g., .07 mole), prepared by platinum-catalyzed addition of distilled monoallyl ether of triethylene glycol to 3-hydroheptamethyltrisiloxane, was added. The resultant solution was heated 1 hour at 85°–90° C. Then the reaction product was neutralized with ammonia gas and was filtered. After stripping off the solvent, a very viscous, brown silicone sulfate was obtained. The composition was $Me_3SiO[NH_4O_3SO(C_2H_4O)_3C_3H_6SiMeO]SiMe_3$.

Aqueous surface tensions of this sulfate at concentrations of 1.0, 0.1 and .01 weight percent were 20.6, 21.6 and 34.6 dynes/cm. at 25° C., respectively. A 1 percent aqueous solution of this sulfate readily wetting polyethylene (590% increase in drop diameter in three minutes). Wetting time for this solution, by the Synthron Tape Method, was 13 seconds.

EXAMPLE 15

When a copolymer of composition $Me_3SiO[Me_2SiO]_{20}[(HOCH_2)_2C(Et)CH_2OC_3H_6SiMeO]_{3.5}SiMe_3$ (0.36 mole of OH) as prepared in Example 2 of the copending application and sulfamic acid (0.36 mole) are reacted in the manner set forth in Example 10 herein, there results a silicone sulfate having the approximate average composition $Me_3SiO[Me_2SiO]_{20}[(NH_4O_3SOCH_2)_2C(ET)CH_2OC_3H_6SiMeO]_{3.5}SiMe_3$ and having surface active properties.

EXAMPLE 16

When a copolymer of composition $Me_3SiO[Me_2SiO]_{8.5}[(HOCH_2)(CH_2\!=\!CHCH_2OCH_2)C(Et)CH_2OC_3H_6SiMeO]_{3.5}SiMe_3$ (0.36 mole of OH) as prepared in Example 3 of the copending application and sulfamic acid (0.36 mole) are reacted in the manner set forth in Example 10 herein, there results a silicone sulfate having the approximate average composition $Me_3SiO[Me_2SiO]_{8.5}[(NH_4O_3SOCH_2)(CH_2\!=\!CHCH_2OCH_2)C(Et)CH_2OC_3H_6SiMeO]_{3.5}SiMe_3$ and having surface active properties.

EXAMPLE 17

When a copolymer of composition $Me_3SiO[Me_2SiO]_{105}[(HOCH_2)(CH_2\!=\!CHCH_2OCH_2)C(Et)CH_2OC_3H_6SiMeO]_{8.8}SiMe_3$ (0.36 mole of OH) as prepared in Example 4 of the copending application and sulfamic acid (0.36 mole) are reacted in the manner set forth in Example 10 herein, there results a silicone sulfate having the approximate average composition $Me_3SiO[Me_2SiO]_{105}[(NH_4O_3SOCH_2)(CH_2\!=\!CHCH_2OCH_2)C(Et)CH_2OC_3H_6SiMeO]_{8.8}SiMe_3$ and having surface active properties.

EXAMPLE 18

When a copolymer of composition $[HOCH_2]_2C[CH_2OC_3H_6SiMe(OSiMe_3)_2]_2$ (0.36 mole of OH) as prepared in Example 7 of the copending application and sulfamic acid (0.36 mole) are reacted in the manner set forth in Example 10 herein, there results a silicone sulfate having the approximate average composition $[NH_4O_3SOCH_2]_2C[CH_2OC_3H_6SiMe(OSiMe_3)_2]_2$ and having surface active properties.

EXAMPLE 19

When a copolymer of composition $HOCH_2C[CH_2OC_3H_6SiMe(OSiMe_3)_2]_3$ (0.36 mole of OH) as prepared in Example 8 of the copending application and sulfamic acid (0.36 mole) are reacted in the manner set forth in Example 10 herein, there results a silicone sulfate having the approximate average composition $NH_4O_3SOCH_2C[CH_2OC_3H_6SiMe(OSiMe_3)_2]_2$ and having surface active properties.

EXAMPLE 20

When a copolymer of composition $Me_3SiO[SiMe_2O]_{8.5}[(HO)_2C_6H_{11}OC_3H_6SiMeO]_{3.5}SiMe_3$ (0.36 mole of OH) as prepared in Example 9 of the copending application and sulfamic acid (0.36 mole) are reacted in the manner set forth in Example 10 herein, there results a silicone sulfate having the approximate average composition $Me_3SiO[SiMe_2O]_{8.5}[(NH_4O_3SO)_2C_6H_{11}OC_3H_6SiMeO]_{3.5}SiMe_3$ and having surface active properties.

EXAMPLE 21

When a copolymer of composition $HOC_6H_{11}[OC_3H_6SiMe(OSiMe_3)_2]_2$ (0.36 mole of OH) as prepared in Example 10 of the copending application and sulfamic acid (0.36 mole) are reacted in the manner set forth in Example 10 herein, there results a silicone sulfate having the approximate average composition $NH_4O_3SOC_6H_{11}[OC_3H_6SiMe(OSiMe_3)_2]_2$ and having surface active properties.

EXAMPLE 22

When a mixture of a copolymer of the composition $(HOCH_2)(CH_2\!=\!CHCH_2OCH_2)C(Et)CH_2OC_3H_6SiMe(OSiMe_3)_2$ and a copolymer of the composition $(HOCH_2)C(Et)[CH_2OC_3H_6SiMe(OSiMe_3)_2]_2$ (0.36 mole total OH in mixture) as prepared in Example 5 of the copending application and sulfamic acid (0.36 mole) are reacted in the manner set forth in Example 10 herein, there results a mixture of silicone sulfates having the approximate average compositions of $(NH_4O_3SOCH_2)(CH_2\!=\!CHCH_2OCH_2)C(Et)CH_2OC_3H_6SiMe(OSiMe_3)_2$ and $(NH_4O_3SOCH_2)C(Et)[CH_2OC_3H_6SiMe(OSiMe_3)_2]_2$ and having surface active properties.

Using the procedures and starting materials described above, the following novel siloxanes are prepared: $Me_3SiO[Me_2SiO]_{20}[NH_4O_3SOC_2H_4OC_3H_6SiMeO]_6SiMe_3$, $Me_3SiO[Me_2SiO]_{20}[NaO_3SOC_2H_4OC_2H_4OC_3H_6SiMeO]_{3.2}SiMe_3$, $Me_3SiO[Me_2SiO]_{8.5}[NH_4O_3SOC_2H_4OC_2H_4OC_2H_4OC_2H_4OC_3H_6SiMeO]_{3.5}SiMe_3$, $Me_3SiO[Me_2SiO]_{105}[NH_4O_3SO(C_2H_4O)_nOC_3H_6SiMeO]_{8.8}SiMe_3$, where n averages respectively 4, 6, 9, 13, 22, 35 and 67, $NaO_3SO(C_3H_6O)_nOC_3H_6SiMe(OSiMe_3)_2$, where n averages respectively 2, 7, 17 and 40, $Me_3SiO[Me_2SiO]_{8.5}[NaO_3SO(C_3H_6O)_{14}(C_2H_4O)_{19}OC_3H_6SiMeO]_{3.2}SiMe_3$, $Me_3SiO[Me_2SiO]_9[(NH_4O_3SOCH_2)_2C(Et)CH_2OC_3H_6SiMeO]_{11.2}SiMe_3$, $Me_3SiO[Me_2SiO]_{20}[(NH_4O_3SOCH_2)_3CCH_2OC_3H_6SiMeO]_{3.5}SiMe_3$, $Me_3SiO[Me_2SiO]_{20}[(NH_4O_3SO)_2C_6H_{11}OC_3H_6SiMeO]_6SiMe_3$, $(NH_4O_3SOCH_2)_2C(Me)CH_2OC_3H_6SiMe(OSiMe_3)_2$, $Me_3SiO[Me_2SiO]_{8.5}[(NaO_3SOCH_2)_2C(C_6H_5)CH_2OC_3H_6SiMeO]_{3.2}SiMe_3$, $NaO_3SOCH_2C(Me)(C_6H_5)CH_2OC_3H_6SiMe(OSiMe_3)_2$, $NaO_3SOCH_2C(Me)_2CH_2OC_3H_6SiMe(OSiMe_3)_2$, NH$_4$O$_3$SOCH$_2$C(Et)[CH$_2$OC$_3$H$_6$SiMe(OSiMe$_3$)$_2$]$_2$,
(NH$_4$O$_3$SOCH$_2$)$_2$C[CH$_2$OC$_3$H$_6$SiMe(OSiMe$_3$)$_2$]$_2$,
NH$_4$O$_3$SOCH$_2$C(C$_6$H$_5$)[CH$_2$OC$_3$H$_6$SiMe(OSiMe$_3$)$_2$]$_2$,
NaO$_3$SOCH$_2$C(Me)[CH$_2$OC$_3$H$_6$SiMe(OSiMe$_3$)$_2$]$_2$,
NaO$_3$SOC$_6$H$_{11}$[OC$_3$H$_6$SiMe$_3$)$_2$]$_2$, NH$_4$O$_3$SOCH$_2$C[C-H$_2$OC$_3$H$_6$ SiMe(OSiMe$_3$)$_2$]$_3$, Me$_3$SiO[Me$_2$SiO]$_{20}$[NH$_4$O$_3$SO(CH$_2$)$_4$CH—O—CHC$_2$H$_4$SiMeO]$_{3.5}$SiMe$_3$,
 　　　　　　　　　　　　　　　　　|　　／
 　　　　　　　　　　　　　　　　CH$_2$—O Me$_3$SiO[Me$_2$SiO]$_{8.5}$[NH$_4$O$_3$SOCH(Me)CH$_2$O(CH$_2$)$_4$CH—O—CHC$_2$H$_4$SiMeO]$_{3.5}$—SiMe$_3$,
 　　　　　　　　　　　　　　　　　　　　　　　　　　|　　／
 　　　　　　　　　　　　　　　　　　　　　　　　CH$_2$—O Me$_3$SiO[Me$_2$SiO]$_{105}$[(NH$_4$O$_3$SOCH$_2$)$_2$CCH$_2$OCHC$_2$H$_4$SiMeO]$_{8.8}$SiMe$_3$,
 　　　　　　　　　　　　　　　　　　　　　＼　／
 　　　　　　　　　　　　　　　　　　　　　CH$_2$O Me$_3$SiO[Me$_2$SiO]$_9$[(NH$_4$O$_3$SOCH$_2$)$_2$CCH$_2$OC(Me)C$_2$H$_4$SiMeO]$_{11.2}$SiMe.
 　　　　　　　　　　　　　　　　　　　　　＼　／
 　　　　　　　　　　　　　　　　　　　　　CH$_2$O The novel water-soluble siloxanes are profoamers, e.g., forming stable foams in aqueous systems, emulsifiers, e.g., for benzene-water systems, and surface tension lowering agents.

The siloxanes of this invention having sodium as the cation, M, can be converted to siloxanes having cations other than sodium by conventional methathetical reactions using chlorides of such other cations, for example, of the formula MCL$_x$. Sodium chloride is produced by the methathesis and the selection of reaction medium should be such that sodium chloride precipitates out while the siloxane reactant, the MCl$_x$ reactant, and the siloxane product remain substantially in solution during the reation. Since, in the metathesis, the siloxane reactant and product and many of the chlorides MCl$_x$ are soluble in toluene and ether while sodium chloride is not, either of these two solvents can be used as the reaction medium. For example, stannous chloride, stannic chloride, potassium chloride, aluminum chloride, and zinc chloride are soluble in ether, which can be used as the medium for the metathetical reaction to convert siloxanes having sodium as the cation M into corresponding siloxanes having stannous, stannic, potassium, aluminum or zinc as the cation M. When the cation M of the novel siloxanes is multivalent and the siloxane has substantially more than one sulfonate siloxy unit, cross-linking can occur through the multivalent cation to provide a three dimensional resin. By similar procedures ammonium and alkyl ammonium siloxane sulfates may be prepared. Cation exchange resins can also be used to replace the cations of the novel siloxanes with other cations.

What is claimed is:

1. A siloxane selected from the group consisting of:
   A. A siloxane containing the sulfatoorganoxyalkylsiloxy unit of the formula:

$$[MO_3SO]_bR\left[\begin{array}{c}R'_x\\|\\C_aH_{2a}SiO_{\frac{3-x}{2}}\end{array}\right]_c \quad (I)$$

wherein M is an alkali metal cation, a is an integer of 2 to 4, x is an integer of 0 to 2, b and c are as hereinafter defined, R' is a linear alkyl group having no more than 18 carbon atoms, R is a trivalent group having the formula:

$$-(-CH_2)_bC(CH_2O-)_c^{R''_{4-b-c}}$$

wherein R'' is a linear alkyl group having no more than 19 carbon atoms, b is an integer of 1 to 3, c is an integer of 1 to 3 and b+c is an integer of 3 and is equal to the valence of said R group; each said sulfate group MO$_3$SO- being bonded to carbon of a carbon to carbon chain of said R group, said siloxane containing 1 to 100 mole % of sulfatoorganoxyalkylsiloxy units of said formula (I) and 0 to 99 mole % of units represented by the formula:

$$Z_zSiO_{\frac{4-z}{2}} \quad (II)$$

wherein Z is a linear alkyl group having no more than 18 carbon atoms, hydrogen, or a monovalent polyoxyalkylene group of the formula DO(C$_y$H$_{2y}$O)$_s$C$_a$H$_{2a}$- wherein D is an alkyl group, y is an integer of 2 to 4, a is an integer of 2 to 3 and s is an integer of 1 to 100, and z has a value from 0 to 3 inclusive; and B. a siloxane containing the sulfatoorganoxyalkylsiloxy unit of the formula:

$$[MO_3SO]_bR\left[\begin{array}{c}R'_x\\|\\C_aH_{2a}SiO_{\frac{3-x}{2}}\end{array}\right]_c \quad (III)$$

wherein M is an ammonium cation and a, x, b, c, R', R, R'' and (b+c) are as defined for formula (I) above, each said sulfate group MO$_3$SO- being bonded to carbon of a carbon to carbon chain of said R group, said siloxane containing 1 to 100 mole % of sulfatoorganoxyalkylsiloxy units of said formula (III) and 0 to 99 mole % of units represented by the formula:

$$Z_zSiO_{\frac{4-z}{2}} \quad (IV)$$

wherein Z is a linear alkyl group or hydrogen and z has a value from 0 to 3 inclusive.

2. A siloxane as defined in part A. of claim 1.

3. A siloxane as claimed in claim 1 wherein M is a sodium cation.

4. A siloxane as claimed in claim 1 wherein Z is a linear alkyl group.

5. A siloxane as claimed in claim 1 wherein R' and Z are methyl groups and R'' is an ethyl group.

6. a siloxane as claimed in claim 1 wherein the

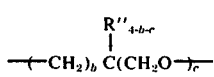

group is a -(CH$_2$)$_2$C(C$_2$H$_5$)CH$_2$O- group.

7. A siloxane as claimed in claim 1 wherein the

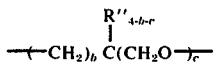

group is a -(CH$_2$)$_2$C(C$_2$H$_5$)CH$_2$O- group.

8. A siloxane as claimed in claim 3 wherein the

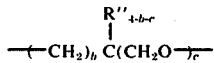

group is a -(CH$_2$)$_2$C(C$_2$H$_5$)CH$_2$O- group.

9. A siloxane as claimed in claim 4 wherein the

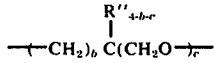

group is a -(CH$_2$)$_2$C(C$_2$H$_5$)CH$_2$O- group.

10. A siloxane as claimed in claim 1 wherein M is ammonium, R' and Z are methyl groups and the

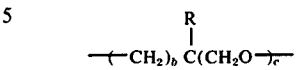

group is a -(CH$_2$)$_2$C(C$_2$H$_5$)CH$_2$O- group.

11. A siloxane as claimed in claim 1 having the average composition [(Me$_3$SiO)$_2$Si(Me)C$_3$H$_6$OCH$_2$]$_2$C(C$_2$H$_5$)(CH$_2$OSO$_3$NH$_4$).

12. A siloxane as claimed in claim 1 having the average composition Me$_3$SiOMe$_2$SiC$_3$H$_6$OCH$_2$C(C$_2$H$_5$)(CH$_2$OSO$_3$NH$_4$)$_2$.

13. A siloxane as claimed in claim 1 having the average composition Me$_3$SiO[(NH$_4$O$_3$SOCH$_2$)$_2$C(C$_2$H$_5$)CH$_2$OC$_3$H$_6$SiMeO]SiMe$_3$.

14. A siloxane as defined in part B of claim 1.

15. A silxoane as claimed in claim 1 having the average composition Me$_3$SiO[Me$_2$SiO]$_{8.5}$[(NH$_4$O$_3$SOCH$_2$)$_2$C(C$_2$H$_5$)CH$_2$OC$_3$H$_6$SiMeO]$_{3.5}$SiMe$_3$.

16. A siloxane as claimed in claim 1 having the average composition Me$_3$SiO[Me$_2$SiO]$_{8.5}$[((C$_2$H$_5$)$_3$NHO$_3$SOCH$_2$)$_2$C(C$_2$H$_5$)CH$_2$OC$_3$H$_6$SiMeO]$_{3.5}$SiMe$_3$.

17. A siloxane as claimed in claim 1 having the average composition Me$_3$SiO[Me$_2$SiO]$_{20}$[(NH$_4$O$_3$SOCH$_2$)$_2$C(Et)CH$_2$OC$_3$H$_6$SiMeO]$_{3.5}$SiMe$_3$.

* * * * *

UNITED STATES PATENT OFFICE
CERTIFICATE OF CORRECTION

Patent No. 3,997,580                    Dated December 14, 1976

Inventor(s) EDWARD L. MOREHOUSE

It is certified that error appears in the above-identified patent and that said Letters Patent are hereby corrected as shown below:

Column 3, line 30, "lyoxyalylene" should be -- lyoxyalkylene --.

Column 3, line 68, the comma "," should be a period -- . --.

Column 15, line 21, the letters "followign" should be deleted.

Column 15, line 40, "nuetralized" should be -- neutralized --.

Column 19, line 28, "methathetical" should be -- metathetical --.

Column 19, line 31, "methathesis" should be -- metathesis --.

UNITED STATES PATENT OFFICE
CERTIFICATE OF CORRECTION

Patent No. 3,997,580   Dated December 14, 1976

Inventor(s) EDWARD L. MOREHOUSE

It is certified that error appears in the above-identified patent and that said Letters Patent are hereby corrected as shown below:

Column 19, line 35, "reation" should be -- reaction --.

Column 20, line 39, in claim 1, "ix" should be -- is --.

Column 21, line 3, in claim 6, "a" should be -- A --.

Column 21, line 10, in claim 7, "1" should be -- 2 --.

Column 22, line 20, in claim 15, "silxoane" should be -- siloxane --.

Signed and Sealed this

Twenty-sixth Day of June 1979

[SEAL]

Attest:

RUTH C. MASON
Attesting Officer

DONALD W. BANNER
Commissioner of Patents and Trademarks